US008292845B2

(12) United States Patent
Del Vecchio

(10) Patent No.: US 8,292,845 B2
(45) Date of Patent: Oct. 23, 2012

(54) DEVICE FOR RENDERING INJECTABLE DERMIS

(75) Inventor: Daniel A. Del Vecchio, Wrentham, MA (US)

(73) Assignee: Lipovera, LLC, North Attleboro, MA (US)

( * ) Notice: Subject to any disclaimer, the term of this patent is extended or adjusted under 35 U.S.C. 154(b) by 0 days.

(21) Appl. No.: 13/181,597

(22) Filed: Jul. 13, 2011

(65) Prior Publication Data

US 2011/0270155 A1 Nov. 3, 2011

Related U.S. Application Data

(63) Continuation of application No. 12/127,329, filed on May 27, 2008, now Pat. No. 8,002,735.

(60) Provisional application No. 60/940,037, filed on May 24, 2007.

(51) Int. Cl.
*A61M 37/00* (2006.01)
*B01F 15/02* (2006.01)

(52) U.S. Cl. .......................................... 604/82; 366/131

(58) Field of Classification Search .................... 604/82, 604/87, 89, 91; 366/131
See application file for complete search history.

(56) References Cited

U.S. PATENT DOCUMENTS

| | | | | |
|---|---|---|---|---|
| 2,477,598 | A | 8/1949 | Hain | |
| 5,425,580 | A | 6/1995 | Beller | |
| 6,736,799 | B1 | 5/2004 | Erbe et al. | |
| 6,916,309 | B2 | 7/2005 | Fangrow, Jr. | |
| 6,936,271 | B1 | 8/2005 | Oliver et al. | |
| 6,942,639 | B2 | 9/2005 | Baugh et al. | |
| 8,002,735 | B2 | 8/2011 | Del Vecchio | |
| 2001/0016750 | A1 * | 8/2001 | Malecki et al. | 606/158 |
| 2004/0186447 | A1 | 9/2004 | Mori | |
| 2006/0058735 | A1 | 3/2006 | Lesh | |
| 2006/0078591 | A1 | 4/2006 | Del Vecchio | |
| 2009/0048558 | A1 | 2/2009 | Del Vecchio | |

FOREIGN PATENT DOCUMENTS

| | | | |
|---|---|---|---|
| WO | WO-2008/148071 | A2 | 12/2008 |
| WO | WO-2008/148071 | A3 | 12/2008 |
| WO | WO-2008/148071 | A9 | 1/2009 |

OTHER PUBLICATIONS

Ellenbogen, M.D., Richard , "The Future of Plastic Surgery is Stem Cells", http://www.makemeheal.com/news/category/plastic-surgery-news/facelift-blepharoplasty/ Oct. 15, 2007 , all.

Lahiany, Sarah , "The Future of Plastic Surgery Is Stem Cells", http://www.makemeheal.com/news/category/plastic-surgery-news/facelift-blepharoplasty/ Richard Ellenbogen, M.D. Oct. 15, 2007 , 3-7.

Moretti, Michael et al., "The Dermal Fillers Revolution", Aesthetic Buyers Guide Jan./Feb. 2006 www.miinews.com Feb. 2006 , 1-12.

(Continued)

*Primary Examiner* — Kevin C Sirmons
*Assistant Examiner* — Bradley Osinski
(74) *Attorney, Agent, or Firm* — Strategic Patents, P.C.

(57) ABSTRACT

Volume filling and/or augmentation are improved by harvesting live dermis from a donor and processing the dermis for re-injection into the donor. A variety of kits, tools, and methods are described for harvesting, processing, and using injectable dermis in volume filling procedures.

20 Claims, 7 Drawing Sheets

OTHER PUBLICATIONS

ISR, , "International Search Report and Written Opinion", for US Patent Application No. PCT/US2008/064804 Jan. 7, 2009.

"U.S. Appl. No. 12/127,329, Notice of Allowance mailed Mar. 18, 2011", , 8.

"U.S. Appl. No. 12/127,329, Notice of Allowance mailed May 13, 2011", , 6.

"U.S. Appl. No. 12/127,329, Non-Final Office Action mailed Dec. 2, 2010", , 8.

* cited by examiner

DEVICE FOR RENDERING INJECTABLE DERMIS

RELATED APPLICATIONS

This application is a continuation of U.S. application Ser. No. 12/127,329 filed May 27, 2008, now U.S. Pat. No. 8,002, 735, which claims the benefit of U.S. Prov. App. No. 60/940, 037 filed on May 24, 2007.

This application is related to U.S. Prov. App. No. 60/617, 448 filed on Oct. 8, 2004 and U.S. application Ser. No. 11/244,321 filed on Oct. 5, 2005.

Each of the foregoing applications is hereby incorporated by reference in its entirety.

BACKGROUND

1. Field of the Invention

This disclosure relates to devices and methods for surgery, and more particularly to volume restoration using injectable dermis.

2. Description of the Related Art

Cosmetic surgeons and the like commonly address contour defects and other volume abnormalities in soft tissues with various volume fillers. However, the volume fillers currently used for reconstructive and soft tissue augmentation all suffer from various drawbacks, many of which are discussed below.

For example, commercially available bovine collagen (derived from enzymatic degradation from bovine hides) lacks structural cross linking. Such collagen lasts as an implant for 4-6 weeks. There is also a concern over the possibility of transmission of Mad Cow Disease ("MCD") using bovine collagen preparations. Human injectable collagen, derived from human fibroblasts in culture, is likewise enzymatically processed to remove cellular material. But due to the enzymatic nature of the process for rendering it injectable, there is significant loss of collagen cross linking and the product lasts a short period of time in the body. In the case of human collagen, there is also a small theoretical potential for viral transmission.

Restylane, a hyaluronic acid preparation, is FDA approved in the United States to augment the deep dermis and lasts 4-6 months. Drawbacks relating to Restylane include its cost per cubic centimeter ("cc") and the need for multiple (3-6) cc's of volume filler in many clinical cases.

Autologous fat is also used for injection into the subcutaneous space and lasts 4-6 months. This method of subcutaneous filler augmentation requires a donor site harvesting procedure and involves over-correction at the insertion site, as there is considerable resorption of fat volume early on due to the destruction of damaged fat cells during the process. This leads to considerable short-term morbidity.

Hydroxyappetite crystals are FDA approved in solid block form for bone interposition grafting. This product is used off-label, and is injected subcutaneously to treat deep facial lines. Persistence of volume has been demonstrated for 12-14 months. Such material is not soft and is easily palpable in vivo and can cause granulomas if injected too superficially. It is not FDA approved for this use.

More permanent fillers such as Gore Tex are inserted as strips subcutaneously and can serve as a nidus for bacteria. Because they are solid sheets they do not allow for dispersion in the subcutaneous space and can cause visible sharp edges under the skin.

Medical grade silicone gel has historically been used as a filler but its use is currently condemned due to long term problems with granuloma formation and an unclear causal association with connective tissue diseases. Fragmented solid silicone microspheres are currently undergoing FDA evaluation for use in bulking the peri-urethral soft tissues in the treatment of urinary stress incontinence.

Internally placed autologous or allograft dermis enjoys existing use in the art for soft tissue structural reinforcement, providing structural stability and volume restoration to tissues subjected to atrophy or abnormal or physiological stress, such as the volume restoration treatment of hemifacial microsomia and the use in peri vesicular slings for urinary incontinence. Autologous dermis grafts have been demonstrated in the medical literature to survive in the body and establish a blood supply from the surrounding donor site, in a similar fashion that externally placed skin grafts do over open wounds. However, dermal sheet grafts are too bulky to be used beneath lines on the face and require access incisions to place. Although many cosmetic procedures involve the removal of excess skin, this skin, containing valuable autologous dermis, is most often discarded.

Despite the array of existing techniques and continued research and experimentation, current approaches have recognized drawbacks, including transience of volume filling, local reactions and undesirable donor sites. Therefore, there remains a need in the art for more satisfactory systems and methods for tissue volume filling and augmentation.

SUMMARY

Volume filling and/or augmentation are improved by harvesting live dermis from a donor and processing the dermis for re-injection into the donor. A variety of kits, tools, and methods are described for harvesting, processing, and using injectable dermis in volume filling procedures.

In one aspect there is provided a method for augmenting volume of a soft tissue. This method involves the delivery of autologous injectable dermis to the soft tissue, or alternatively, allograft dermis. The method involves the serial mechanical cubing of the material, and successively fragmenting, mincing or micronizing the material. The delivery step can be performed by a standard syringe injection technique. In one disclosed embodiment the injection material is minced into relatively large micrografts, while in another embodiment it is highly micronized before delivery it to the soft tissue. The soft tissue is selected from the group consisting of the deep intradermal space, subdermal space, subcutaneous space, submucosal space, periurethral space and hypopharyngeal space. The particular size of the autologous injectable dermis therefore varies on the volume requirements of the target are to be treated and the location in the soft tissue.

In another aspect there is provided a method of treating subcutaneous volume deficiency in, for example, volume loss in the face, lips, cheeks, penis, and bulking of the peri-laryngeal and peri-urethral areas comprising the steps of processing harvested uniform-thickness sheets of autologous dermis, processing the material employing manual or machine operated mechanical methods and devices, serially processing the material to achieve the desired viscosity and particle size for injection, and; and transplanting the material into the area being treated via syringe and needle injection.

In a method disclosed herein, one or more therapeutic substances may be added to the autologous injectable dermis prior to the implantation thereof. The therapeutic substances may include one or more of the following: growth factors, differentiation factors, hydrogels, polymers, antibiotics, anti-inflammatory medications, or immunosuppressive medications. The autologous injectable dermis may be injected into the area being treated through a needle and syringe. The autologous injectable dermis may be percutaneously or transmucosally injected into the area being treated.

In another aspect there is disclosed herein devices for fragmenting and morsellizing autologous dermis that include one or more single or double edged stationary cutting blades placed at an angle to the direction of flow within a lumen of a disposable or autoclavable cutting chamber connector that attaches to two opposing syringes by twist lock or by another means, whereby the material passing from syringe to syringe under pressure and by pneumatic action is forced though the lumen of the cutting chamber connector, across the stationary cutting blade(s). This pithing action of the material passing across the blade, and not the blade passing through the material, is a mechanical action that renders the autologous dermis material, with each successive cycle, more and more into a pliable, injectable liquid form.

Other devices and methods are disclosed including various fragmenting and morsellizing systems and methods for processing live dermis and/or fat into an injectable form, along with additives and other handling steps related thereto.

BRIEF DESCRIPTION OF THE FIGURES

The invention and the following detailed description of certain embodiments thereof may be understood by reference to the following figures.

DETAILED DESCRIPTION

The following description relates to systems and methods for processing and implanting dermis (such as the injectable micrograft autologous dermis described below) as a filler material for augmenting tissue volume. As used herein, the term “augmenting” refers to both restoring abnormal contours to a more normal state for cosmetic or reconstructive reasons, and adding to the volume of an existing soft tissue space for cosmetic or reconstructive reasons. As described herein, volume enhancement includes cosmetic subcutaneous and intramuscular volume enhancement of the face, lips, and cheeks, volume enhancement for the treatment of age related and pathologic soft tissue atrophy, cosmetic volume enhancement of the breast and penis, bulking of the periurethral soft tissues for the treatment of urinary stress incontinence and for urinary incontinence post prostatectomy, and bulking of the peri-laryngeal areas in the case of vocal cord dysfunction. The following description also sets out several embodiments of suitable methods and devices for processing autologous dermis into forms suitable for augmenting tissue volume. While a particular type of volume enhancement may suggest certain donor sites, additives, processing specifications (e.g., particle size, viscosity, total volume, etc.) to one or ordinary skill in the art, the following details are provided without any loss of generality, and the systems and methods disclosed herein may be suitably adapted to a wide range of applications for processing and injecting dermis into a donor.

Throughout this description reference is made to the implantation of autologous dermis. However, it will be understood that many of the systems and methods described herein may be applied readily to other materials such as commercially available collagen matrix preparations, allograft dermis, and the like.

Figure 1:
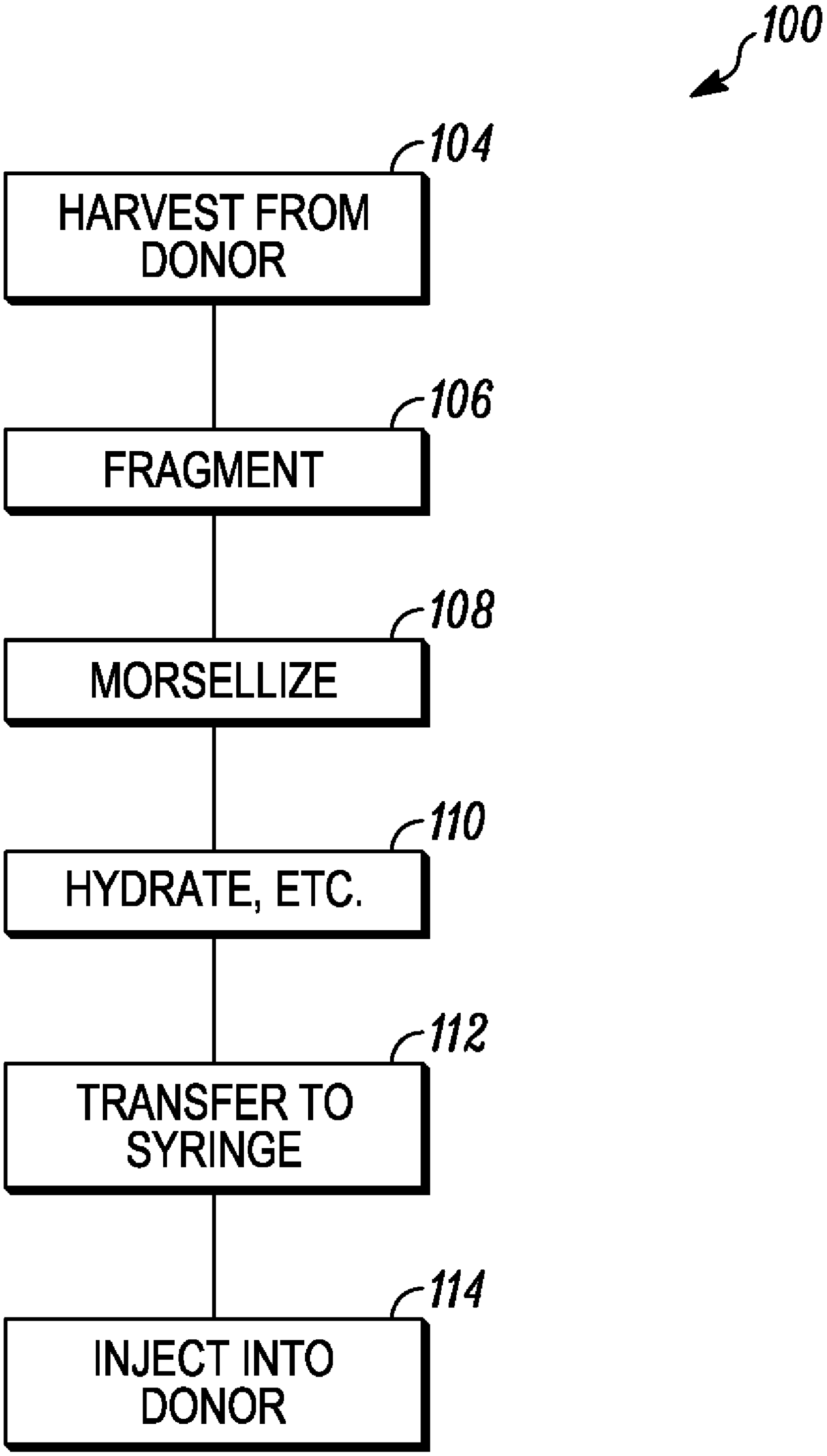
FIG. 1 shows a method for processing autologous dermis into an injectable form.

FIG. 1 shows a method 100 for processing autologous dermis into an injectable form.

Processing may begin with harvesting, as shown in step 104, to provide live dermis. In this step, a substantially uniform thickness sheet of human autologous dermis may be obtained from a human donor in a sterile, viable form using a harvesting device such as a skin grafting harvesting knife or a dermatome (or power-assisted dermatome) or the like for epidermal skin grafting. Harvesting may include, for example, placing a temporary device such as a tissue expander or a Foley catheter beneath the dermis to facilitate harvesting dermis above the temporary device. The temporary device may render dermis immobile or turgid to facilitate harvesting. The sheet of dermis may be removed with no epidermal layer.

Such sheets may range in size depending on the clinical application and on the volume of autologous injectable dermis needed, as well as the availability of the donor area. In one aspect, a preexisting scar such as a caesarean section scar can be revised to act as a donor site for autologous dermis with minimal morbidity. It will be understood that the importance of thickness and the importance of maintaining uniformity of thickness when harvesting will depend upon the donor site, the subsequent processing steps, and other factors. Any variations suitable for use in a donor-to-donor transplantation as generally described herein may be employed without departing from the scope of this description.

In another aspect, the harvesting device may yield dermis in small, minced particles of epidermis. In embodiments, donor fat may also or instead be harvested. Techniques for harvesting fat are well known in the art and any such techniques may be suitably employed to obtain donor fat for use in the methods and systems described herein. In one aspect, fat may be separately harvested, processed, and transplanted. In another aspect, fat and dermis may be separately or collectively harvested and then processed together for concurrent transplant. All such variations are intended to fall within the scope of this disclosure. It will be further understood that while this disclosure focuses on human treatment, the methods and systems described herein may also be suitably adapted to a wide range of other animal treatments.

After harvesting, the harvested dermis may be processed into an injectable form as described below in a series of particular steps. However, it will be understood that the order of the steps may be varied (such as when filler is added), or steps may be omitted or added, or any one of the depicted steps may be modified, without departing from the scope of this disclosure provided that the processing steps yield an injectable form of autologous dermis. This includes techniques such as hand held or mechanical rotary milling, chopping and rasping. By processing the dermis under aseptic sterile conditions immediately after harvesting, the process may increase potential for autograft survival. Further, techniques that substantially avoid enzymatic digestion of dermis may retain viable fibroblasts, a microvascular anatomy, and cross linked collagen with an intact matrix architecture, thereby allowing fibroblasts and blood vessels in a recipient area to undergo cellular in-growth and remodeling, native collagen formation, and a potentially permanent volume fill.

As shown in step 106, the method may proceed to fragmenting. In this step, the harvested sheet of autologous dermis may be processed using, for example, conventional surgical instruments and methods to cut the live dermis and/or other harvested material into smaller pieces. For example, the sheet of dermis may be processed by meshing, i.e., rolled through a mesh roller or other skin graft mesher or graft expanding device. In one embodiment, the dermis may be fragmented by passing repeatedly through a skin graft mesher or other mesh roller at varying angles. Successive passes at, for example, right angles through a skin graft mesher or mesh roller will yield dermal fragments ranging in size from 1-5 millimeters in diameter, a size useful for subsequent processing as described herein. Still more generally, any technique for fragmenting harvested dermis into smaller pieces may be employed as an intermediate processing step.

Fragmenting may also include mincing dermis with a pair of scissors; a process that may be facilitated by the pair of scissors that are described in more detail below; and that include a hole and a syringe coupling on one blade. With this device, dermis can be held in a syringe barrel and delivered to the opposing scissor blades in a controlled manner during mincing.

As shown in step 108, the method may proceed to morsellizing, which generally refers to any technique for processing the dermis fragments into a size and shape suitable for injection, such as by cutting the fragmented material repeatedly by one or more cutting blades until the dermis is reduced to a size suitable for injection.

In one embodiment, fragmented autologous dermis can be inserted into the barrel of a high-pressure syringe and attached to the cutting chamber device described below. With two such syringes attached the each end of the reciprocal cutting chamber device, morsellization can be performed to process the autologous dermis into a more liquid, injectable form. This device can be operated manually by compressing the dermis (along with any additives) through the cutting chamber with alternate depression and release of the plungers of two opposing syringes to achieve bi-directional flow through the cutting chamber.

Still more generally, a variety of manual and mechanized techniques may be employed to apply pressure to a volume of fragmented dermis (and any additives) to drive the material past one or more cutting surfaces. Thus for example, compressing material on one side of the cutting chamber with a suitable pump, such as a unidirectional continuous flow pump or peristaltic pump, can propel the flow of material. In this embodiment, material may circulate repeatedly through the cutting chamber in a unidirectional motion driven by the pump motor or the like. In another embodiment, reciprocating motion for two opposing syringes can be generated by a motorized device, which may be adapted to securely hold two syringes and controlled in any suitable fashion, such as by delivering reciprocating motion at a specified speed, a specified number of times, or with the addition of pressure or force sensors, until a desired viscosity (or resistance to linear motion, as a proxy for viscosity) is reached. The number of cycles of transfer of material unidirectionally (circulating) or bi-directionally (to and fro) through the cutting chamber further morsellizes the material and reduces the particle size and viscosity of the fully processed autologous injectable dermis. In one aspect, the number of cycles may be specified and assumed to result in a target particle size. In another aspect, the pressure required to pass the material through the cutting chamber may be used to determine when a target for particle size or viscosity has been reached.

Still more generally, while the use of dual, reciprocating syringes provides one convenient mixing apparatus using readily available, disposable surgical devices, a variety of other morsellizing techniques may be employed provided they meet the general requirements for live dermis injection, i.e., that they are quick, sterile, and leave live cells in the resulting, processed material.

The cutting chamber, which may for example be any of the cutting chambers described below, can be reusable. For example, the cutting chamber may be an autoclavable device made of stainless steel, with new blades being used each time to maintain good edge sharpness and/or maximize cutting efficiency. Alternatively, the cutting chamber can be disposable. For example, the cutting chamber (also referred to below as a coupling device where the same device provides a lumen with blades for cutting and serves to couple together two opposing syringes) may be fabricated from plastic using injection molding or other mass production techniques suitable for use with medical equipment, and can house a single use blade or blades in any of the blade configurations described below.

Numerous additives may be provided during, before, or after the morsellization process. This may include the addition of saline or therapeutic substances both of which are described in greater detail below. This may also, or instead, include the use of other additives for volume filling, therapeutic effect, and/or to increase lubrication and decrease flow friction during morsellization or injection (or both). By way of example and not limitation, additives may include antibiotics, collagen, lidocaine, epinephrine, hyaluronidase, and a hyaluronic acid base filler such as Restylane, Juvederm, and Captique. Another useful additive is autologous fat. Autologous fat may be added to improve flow characteristics rendered by the lipid nature of the fat cells. Autologous fat may also provide a softer feeling autologous filler. Autologous fat may also promote beneficial effects of dermal fibroblasts in contact with mature adipocytes and with pre-adipocytes.

Morsellization may be used to yield dermis (or other) particles of a variety of sizes. The size and shape of particles used for injection may vary substantially. In one aspect, particles having a volume of up to 2 cubic millimeters are employed. In another aspect, particle having a diameter ranging from 50 to 2000 microns are employed. In one aspect, particle size is selected to preserve live dermis within substantially all of the particles. In general, particles may have regular shapes (such as cubes or spheres) or irregular shapes of any form. Still more generally, any dermis particles that can be handled, injected, and provide the desired therapeutic or cosmetic effect at a target site may be employed consistent with the systems and methods described herein. In one aspect, dermis may be processed into small clumps of fibroblasts, complex fragments of fibroblasts, and other dermal cells embedded in a collagen matrix.

As shown in step 110, hydration may be performed, along with other miscellaneous processing steps that improve injectability, improve handling, maintain live cells, and the like. It will be understood that while depicted in FIG. 1 as a separate step, hydration and other miscellaneous processing steps may suitably be combined with other steps, such as where saline is added to dermis during morsellization. All such variations as may be suitably employed in preparing injectable dermis are intended to fall within the scope of this disclosure.

For example, because interstitial fluid is compressed out of the sheet of autologous dermis during fragmentation, a volume of sterile normal saline or physiologic solution may be added to the fragmented or morsellized autologous dermis via the syringes of the cutting chamber device before, during, or after morsellization. It will be understood that, where the dermis has been morsellized to a desired particle size, subsequent mixing with saline or the like will preferably be performed without the cutting chamber, and a syringe coupling device without blades may be provided for this purpose. In other embodiments, re-hydration during morsellization may reduce friction and allow for smoother flow through the cutting device. Rehydration with buffered physiologic solution may also protect the autograft from desiccation and maintain desired pH, improving graft survival.

Re-hydration using varying volumes also allows for customization of flow and viscosity by varying the amount of sterile saline or physiologic solution to be used in the mixture. A ratio by volume of 1 part of sterile saline or physiologic solution to 4 parts fragmented or morsellized autologous dermis results in a thicker, more viscous injectable material that may be beneficial in deep tissues, whereas greater than equal parts of sterile saline or physiologic solution to fragmented autologous dermis results in a more diluted mixture that flows through a smaller gauge needle, and can be used in a more superficial location in the subcutaneous space or deep dermis. Thus the ratio may be adjusted to achieve a desired viscosity or flow according to the desired handling properties, the target site for injection, and so forth. Variations in the ratio also allow alteration of the volume of the dermis material transferred, thus allowing a surgeon to insert more or less autologous injectable dermis into the subcutaneous, deep dermal, peri-laryngeal, or peri-urethral space.

Another useful auxiliary step is cooling. Cooling of the cutting chamber and/or syringes or other hardware may reduce cell metabolism, improving graft survival. Cooling may be achieved by actively cooling the equipment used during handling of the dermis, or by using cooled saline or the like as an additive as generally described above.

As shown in step 112, the harvested and processed tissue may be transferred to a syringe for injection. In general, this may be any syringe suitable for use in surgical volume enhancement as generally described above.

As shown in step 114, the processed material may be injected. This may include, for example, injecting into one or more of nasolabial folds, lips, cheeks, malar area, chin point, peri-urethral space for urinary incontinence, and peri-laryngeal space for partial vocal cord dysfunction. The injection may also or instead include a percutaneous injection. In certain applications, saline solution may be injected beneath the dermis or into the dermis to render it turgid prior to injection of the injectable dermis. A number of therapeutic and cosmetic applications are described in greater detail below. Once in the body, the autologous dermis (along with any additives such as those described above) acts like conventional dermis or epidermal grafts to allow the in-growth of blood vessels and/or host human fibroblasts.

To minimize bruising and bleeding in the dermis and the subcutaneous tissues that could act as impediments to graft survival, the autologous injectable dermis may be inserted through a small hole in the skin using a large bore 14-18 gauge needle. Upon advancement or withdrawal of the needle, the material is injected, laying down, in some instances, parallel tubes of material into position, thereby increasing volume where desired.

The subcutaneous space in the facial region varies in fat content. Also, age-related and disease-related volume loss varies from individual to individual. Thus, in one embodiment, autologous injectable dermis is inserted into the nasolabial folds and lip and cheek regions in varying amounts. The injection needle can be directed into the subcutaneous space percutaneously or transmucosally via stab incisions or needle insertion into the perioral or labial mucosa.

The autologous injectable dermis may be morsellized to allow insertion into the subcutaneous, peri laryngeal or periurethral area through a 14-20 gauge needle. With respect to smaller particle size autologous injectable dermis, the increased surface to volume ratio of the autologous dermal micrografts may also aid in the ability of the fibroblasts and other dermal elements to survive by diffusion of oxygen from the surrounding recipient tissue, with neovascularization occurring in 4-7 days. The smaller particle size of the autologous injectable dermis may also mitigate visible and palpable lumpiness due to a smoother diversification of volume injected.

Once in the body, the autologous injectable dermis further hydrates by imbibing fluid from the surrounding area. In the case of the subcutaneous areas in the face, the subsequent hydration helps to restore subcutaneous volume and further enhance the treatment of the volume deficient area. Additional therapeutic substances may be added, including tissue growth or differentiation factors (recombinant generated morphogenetic proteins, PDGF, TGF-.beta., EGF/TGF-.alpha., IGF-I, PFGF, etc.), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, and the like, with known therapeutic effect, as well as donor fat where appropriate for an injection site. These additional substances may or may not contribute to rehydration, depending upon efficacy, initial versus final volume, and so forth.

Autologous injectable dermis may be used as a tissue volume filler in cosmetic and reconstructive surgery, in dermatology, in urology, in otolaryngology, and in similar medical specialties. According to the methods disclosed herein, this material may be used as a volume filler by injection. For example, autologous injectable dermis as a subdermal filler may be used in the form of an injected strip laid down subjacent to the nasolabial folds for treatment of depressions of the nasolabial folds, in the form of strips tunneled beneath the lip vermillion via stab incisions in the oral commissures, and in the form of strips injected subjacent to the corrugator muscles to replace volume in those procedures that weaken these muscles, for the purpose of reducing forehead wrinkles.

Injectable dermis may be employed in numerous treatments, a number of which are set out below by way of illustration and not limitation. The systems and methods disclosed herein may be used to place autologous injectable dermis subdermally via small injections in the skin to provide volume enhancement of the face in developmental maladies of facial fat and muscle volume atrophy. Conditions suitable for this treatment include, but are not limited to, Romberg's Hemifacial Atrophy, and facial lipodystrophy associated with HIV treatment, namely protease inhibitor therapy. The systems and methods disclosed herein may be used to place autologous injectable dermis subdermally in strips and locations in the nasal region to provide volume enhancement of the nose in situations where non-surgical nasal grafting is desired to provide volume enhancement. The systems and methods disclosed herein may be used to place autologous injectable dermis subdermally in strips and pieces in the cheek and peri-orbital region to provide volume enhancement of the cheek and peri-orbital soft tissues in situations where cheek and lower eyelid volume enhancement is desired to provide aesthetic enhancement. The systems and methods disclosed herein may be used to inject autologous injectable dermis subdermally in the neck and midface region to provide mechanical suspension of the neck, cheek and peri-orbital soft tissues in situations where neck, cheek and peri-orbital soft tissues suspension and elevation is desired to provide aesthetic enhancement.

In one aspect, disclosed herein is a method of treating a volume-deficient area of the face, cheek, lips, penis, peri-laryngeal, and/or peri-urethral tissue through the transplantation of morsellized, cubed or micronized autologous injectable dermis, such as into a corresponding subcutaneous, deep dermal region where appropriate. In other embodiments, other commercially available collagen matrix preparations, such as embryonic bovine matrix, or autograft dermis or allograft dermis, or a combination of the foregoing may be combined with injectable dermis for implantation. In other embodiments, donor fat may similarly be employed.

In still other embodiments, the systems and methods disclosed herein may be used to place autologous injectable dermis submucosally and/or intramuscularly via needle insertion in the peri-laryngeal and pharyngeal soft tissues to provide bulking and volume enhancement of the peri-laryngeal and pharyngeal soft tissues in situations where bulking materials are desired in the treatment of vocal cord paralysis and in speech disorders related to cleft palate deformities.

Disclosed herein are systems and devices for preparing autologous injectable dermis into forms suitable for use in the aforesaid methods. Using these systems, devices and related methods, autologous injectable dermis may be morsellized, cubed, or rendered into particulate form, suitable for injection for volume enhancement. The disclosed device may further be useful for treating commercially available collagen sheets such as embryonic bovine matrix or allograft dermis, morsellizing, cubing or rendering these tissues into particulate form for injection for volume enhancement. The disclosed device may be used to provide reliable, morsellization, and size reduction of autologous dermis, embryonic bovine matrix and allograft dermis, such preparations being useful either for injection or for other similar techniques to provide soft tissue volume enhancement. Standard embryonic bovine matrix, for example, is derived from the hides of fetal cows and is commercially available in sheets as small as 5×6 cm wide and 0.5-1.5 mm thick, and as large as 10×15 cm wide and 0.5-1.5 mm thick. Allograft and autograft dermis is harvested in a variety of sizes depending on clinical availability.

Autologous injectable dermis has been used in a series of ten patients with volume loss in the lips or in the nasolabial folds. Sheets of autologous dermis, harvested at the time of processing, were fragmented, morsellized and liquefied using the aforementioned techniques and devices. Using sterile aseptic technique the autologous injectable dermis was injected in the lip and nasolabial folds either at the time of a concomitant procedure done under general anesthesia, or using local anesthesia in an outpatient, office setting.

Having described a general process for harvesting and processing dermis for injection, a scissor for facilitating fragmenting and/or morsellizing of dermis material is now described in greater detail.

Figure 2:
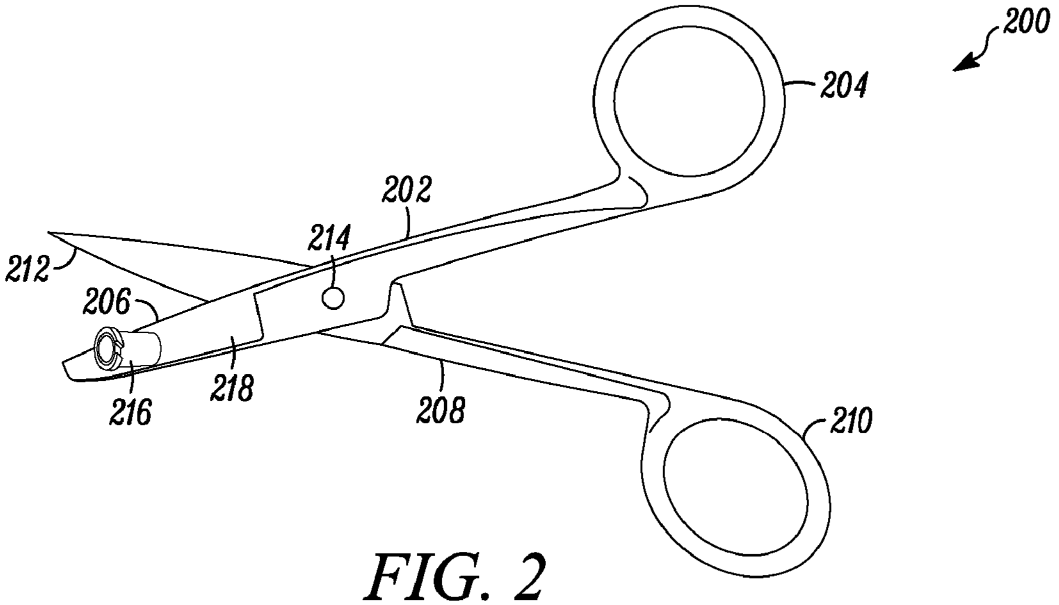
FIG. 2 shows a scissors with a coupling attachment.

FIG. 2 shows a pair of scissors with a coupling attachment. The scissor device 200 may include a first blade 202 with a handle 204 and a cutting edge 206, a second blade 208 with a handle 210 and a cutting edge 212, a pivot 214. A connector 216 such as a Luer Lock may be provided for coupling to a syringe such as an inflow syringe with a plunger and a barrel, or any other suitable syringe or other device for delivering material through the hole. In general operation, the scissor device 200 is operated like a conventional scissors, with the opposing blades 202, 208 pivoted about the pivot 214 into and out of contact to create a shearing action between the first cutting edge 206 and the second cutting edge 212. With a syringe of dermis or other material attached to the connector 216, material may be delivered through a hole (not shown) in the blade 208 while repetitively shearing the material with an ordinary scissor motion as the material exits. The scissor 200 may be formed of an autoclavable or other suitable surgical material such as stainless steel. In other embodiments, the scissor 200 may be disposable, and may be formed of a suitably hard plastic or the like. More generally, any biocompatible or surgical material, or collection of materials may be employed, provided they offer sufficient structural integrity to support a syringe connector and scissor blades, and are capable of retaining a sufficiently sharp cutting edge for the intended purpose.

The connector 216, also referred to herein as a coupling attachment or the like, may be permanently (e.g., with a weld or the like) or temporarily (e.g., with threads or a friction fit) affixed to an exterior surface 218 of the blade 208 of the scissors 200, and aligned with the hole through the blade 208. Thus the connector 216 may secure a syringe in a position to deliver material through the hole. While a generally circular shape for the hole is consistent with the exit orifice of a conventional syringe, it will be understood that other shapes may be suitably employed to extrude material in different shapes such as a ribbon, a square, a rectangle, or multiple different shapes, and combinations of the foregoing.

By operating the scissor blades during the extrusion of material, the material may be conveniently chopped into a finer particle size. This process may be repeated a number of times. In one embodiment, a collection of different coupling attachments and/or scissors with holed blades may be employed to provide a progressively smaller series of exit chambers for increasingly refined cutting. In another aspect, the scissors may have a number of holes and/or coupling attachments to accommodate multi-barrel syringes or multiple syringes. In other aspects, the holes and coupling attachments may be positioned at various locations in the scissors blade, including for example positions near or overlapping the cutting surface such that the hole forms a semi-circle or other partial arc in the blade's cutting edge.

Figure 3:
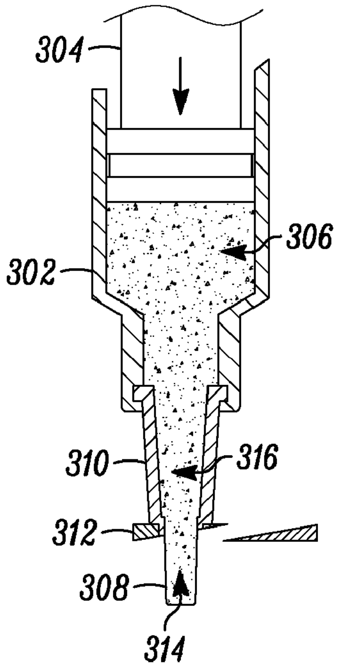
FIG. 3 shows a syringe with a plunger and a barrel containing a material for extrusion.

FIG. 3 shows a syringe 302 with a plunger 304 and a barrel 306 containing a material 308 for extrusion. The syringe 302 is coupled to a connector 310 on a blade 312 of a scissors. As shown, the blade 312 has a lumen 314 (also referred to herein as a hole) for delivering the material 308 from the syringe 302 when the plunger 304 is depressed. Similarly, the connector 310 includes an interior region or lumen 316 that combines with the lumen 314 of the blade 312 to provide a common lumen for passage of material from the interior of the barrel 306 out through the blade 312. As noted above, the connector 310 may be a Luer Lock, and/or may be formed of stainless steel or any other autoclavable material. This common lumen or the lumen 314 of the blade 312 and the lumen 316 of the connector 310 may have an interior diameter between 1 mm and 3 mm, or between 0.5 mm and 3 mm, or any other size suitable for extrusion of material as generally described herein.

Figure 4:
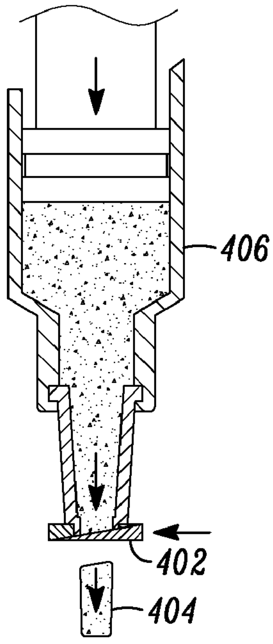
FIG. 4 shows the operation of an opposing blade to cut through the material extruding from the syringe.

FIG. 4 shows the operation of an opposing blade 402 to cut through the material 404 extruding from the syringe 406. It will be understood that, while a particular angle of the blade 402 is depicted, this angle is for illustrative purposes only, and that any angle of the blade 402 relative to the hole and the opposing blade may be suitably employed, provided the opposing blades can cooperate to cut material that is extruding from the syringe 406.

Having described a scissor for facilitating fragmenting and/or morsellizing of dermis material, a dual-syringe system for mechanically morsellizing dermis, additives, and/or other materials is now described in greater detail.

Figure 5:
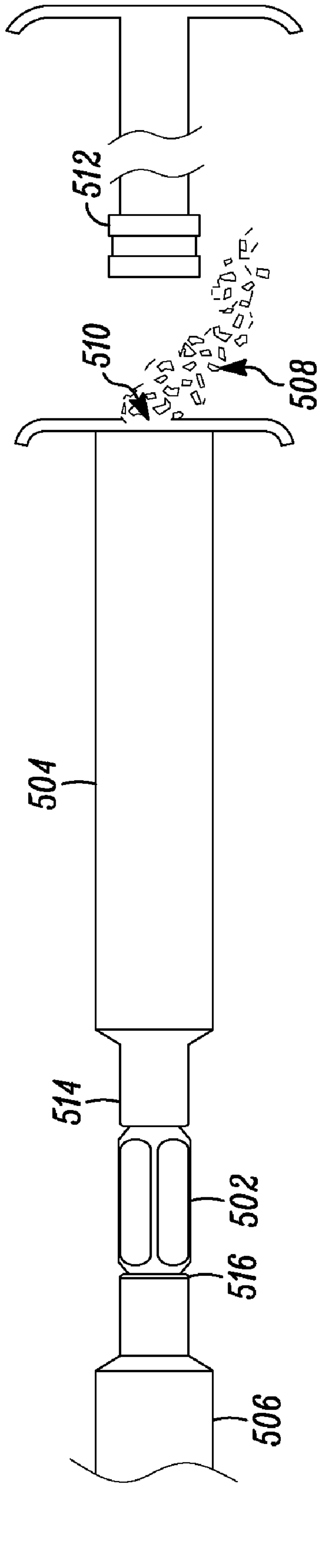
FIG. 5 shows two syringes coupled through a coupling device.

FIG. 5 shows two syringes coupled through a coupling device. In general, a coupling device 502 serves to interconnect a first syringe 504 and a second syringe 506 and provide a lumen (not shown) coupling the interior of the syringes 504, 506 and permitting the passage of material therethrough. Each syringe has a coupling 514, 516 adapted to connect to the coupling device 502, which connection may take any of the numerous forms described herein. Material 508 such as the fragmented dermis and any additives as described above may be added to the interior 510 of the first syringe 504 and a plunger 512 may be inserted into the interior 510 to apply pressure to the material 508, thus pushing the material through the connector 502 and into the second syringe 506.

As noted above, the coupling device 502 may include two co-axial connectors such as Luer Locks to connect to either or both syringes. The coupling device 502 may also, or instead, employ any threaded connector, twist lock, friction fit, or any other connector suitable for use with the syringes described herein. The co-axial connectors may also, or instead, include glue, epoxy, or any fastener or fastening technique that permanently attaches the coupling device 502 to either or both syringes. The two co-axial connectors may connect two syringes through an interior volume of the coupling device 502, with the interior volume including one or more blades as generally described below. When connected in this fashion, a material may be morsellized by passing back and forth through the interior volume of the coupling device 502 (and the blade(s) therein) with a motion imparted by reciprocal motion of opposing syringe plungers. Although not depicted in the following drawings, it will be understood that in certain embodiments, one or more additional ports may be provided to the coupling device. For example, a third Luer lock connector may be added to form a "T". The third connector may accommodate a third syringe or other material source for incrementally adding any of the additives described above including saline for hydration as well as any other therapeutic additives such as tissue growth factor, antibiotics, and so forth. Unless additional morsellizing is desired for materials entering through the third port, this connector need not lie directly in or near the portion of the path joining the first two syringes that contains the cutting blades. However, in alternative embodiments, this third port may also include one or more cutting blades for morsellizing material passing therethrough.

Figure 6:
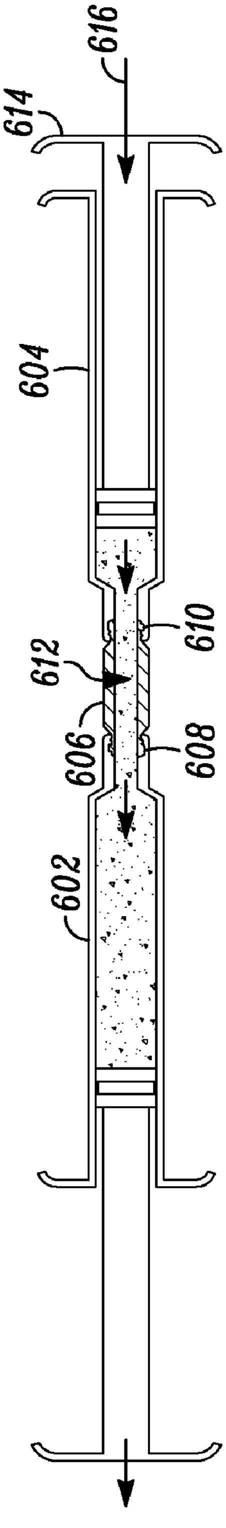
FIG. 6 shows two syringes coupled through a coupling device.

FIG. 6 shows two syringes coupled through a coupling device. As depicted, a first syringe 602 and a second syringe 604 are coupled by a coupling device 606 having a first connector 608, a second connector 610 and a lumen 612 for passage of material between the syringes, all as generally described above. In operation, material is moved into the first syringe 602 by depressing a plunger 614 as indicated generally by an arrow 616, and corresponding arrows showing complementary movement of the material and a plunger for the first syringe 602. The cutting blades are omitted from this figure for illustrative purposes, however it will be understood that any number and arrangement of blades may be provided within the lumen 612 for morsellizing material passing therethrough.

Figure 7:
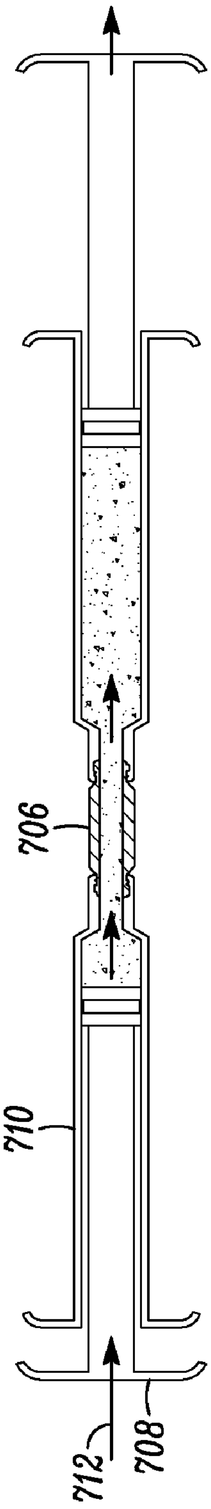
FIG. 7 shows two syringes coupled through a coupling device.

FIG. 7 shows two syringes coupled through a coupling device. In this figure, direction of material flow has been reversed from FIG. 6, and material is pushed back through a coupling device 706, which may be any of the coupling devices described above, by operation of a plunger 708 on a first syringe 710, as indicated by an arrow 712.

By operating the two plungers of the two syringes in a back and forth motion, the material may be forced repetitively through a path through the interior volume or lumen of the coupling device. In general, this back and forth, complementary motion of plungers on two coaxial syringes coupled through a coupling device can be easily effected by opposing index fingers or thumbs of two human hands, with other fingers supporting the syringes and or coupling device. By placing one or more cutting blades in this path, as illustrated below, particle or tissue fragment size within the material may be successively reduced to any size and/or consistency for a desired use. Thus in one aspect, a method as described herein may include morsellizing by repetitive passage through a lumen containing one or more intraluminal blades, such as any of the blades described in greater detail below. Without a loss of generality in the following description, the intraluminal blades may, for example, have an edge transversely angled to the direction of flow, or an edge that is normal to the direction of flow, or some combination of these.

While the illustration depicts a coupling device having an interior volume axially aligned with the barrels of the coupled syringes, this arrangement is not strictly required. In one aspect, the interior volume may include any straight or curved path, provided the path couples the syringes to form a single interior volume. In one embodiment, the syringes may be coaxial while the interior chamber has curving path. It will also be noted that, while the syringe plungers may be coaxial to permit easy manipulation, other arrangements may be employed. For example, the axes of the plungers may be angled at a right angle or a more acute angle and still provide for easy reciprocal operation by two thumbs of a user. All such variations are intended to fall within the scope of this disclosure.

Figure 8:
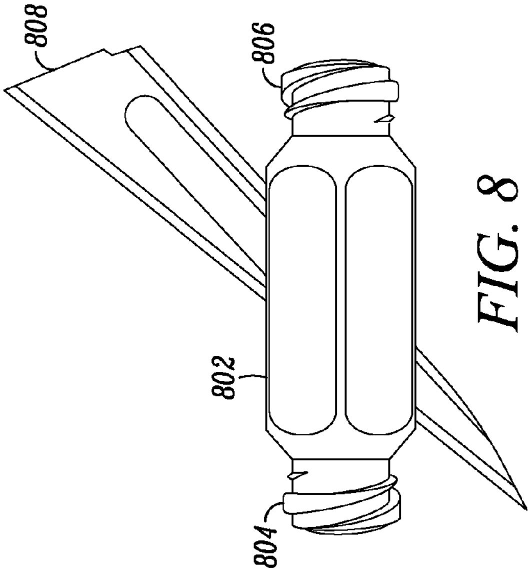
FIG. 8 shows an external view of a coupling device and a blade.

FIG. 8 shows an external view of a coupling device and a blade. In this embodiment, a coupling device 802 includes connectors 804, 806 for syringes or the like, and provides slits (not shown) to removably receive a surgical blade 808. As depicted, a blade 808 such as any conventional surgical blade may be passed through the lumen or interior volume of the coupling device 802 at a location that crosses a path of material passing through the lumen during a motion such as the reciprocal motion described and shown above.

Figure 9:
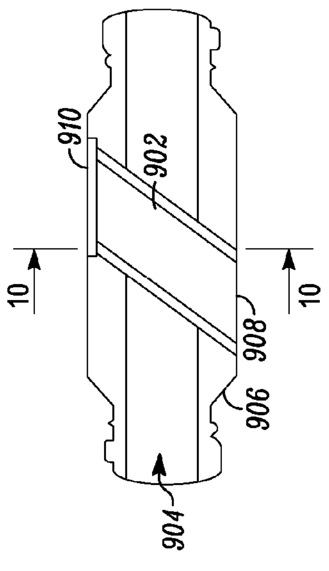
FIG. 9 shows a cross-sectional view of a coupling device and a blade.

FIG. 9 shows a cross-sectional view of a coupling device and a blade. As depicted, the blade 902 may be supported within an interior volume 904 (also referred to herein as a lumen) of the coupling device 906 by opposing slits 908, 910 in an exterior wall of the coupling device 906. As shown, the blade may be advantageously placed at an angle with respect to an axis passing through the interior volume 904 in order to improve the cutting action of the blade and/or reduce flow resistance as a material passes the cutting surface in a direction of the axis. It will also be appreciated that the blade 902 may be a single-edge blade or a dual-edge blade. A dual-edge blade may advantageously present a cutting surface in both reciprocal directions of material flow through the interior volume 904. In one aspect, the slits 908, 910 may be shaped and sized to precisely accommodate the blade 902, so that very little leakage is possible for the pressurized material within the interior volume 904. In other embodiments, a loose fit may be provided, with seepage through the slits 908, 910 permitted during reciprocal motion of the syringes. In another aspect, a surgically suitable, sterile sealing material may be employed around the edges of the blade 902 to prevent or mitigate seepage. The sealing material may be applied after the blade 902 is fit through the interior volume 904; or may be a plastic material or the like positioned within the slits 908, 910 to self-seal when the blade 902 is inserted through the lumen; or may or seal with an application of heat, pressure, light, or the like after insertion of the blade 902.

Figure 10:
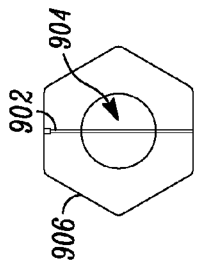
FIG. 10 shows an axial cross-section of the coupling device viewed from the perspective indicated in FIG. 9.

FIG. 10 shows an axial cross-section of the coupling device viewed from the perspective indicated in FIG. 9. As shown a single blade 902 is positioned across the lumen or interior volume 904 of the coupling device 906 in order to cut material passing thereby.

Figure 11:
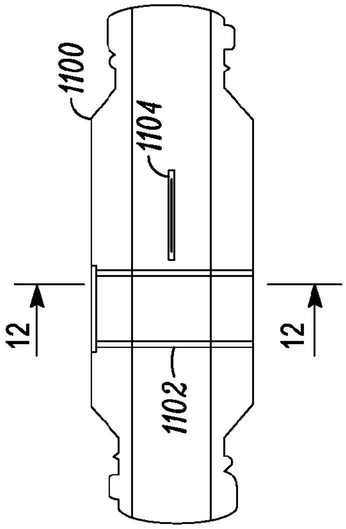
FIG. 11 shows a cross-sectional view of a coupling device and two blades.

FIG. 11 shows a cross-sectional view of a coupling device and two blades. The coupling device 1100 may include a first blade 1102 and a second blade 1104, each inserted through slits in the coupling device 1100 as generally described above. The blades 1102, 1104 may, for example, be offset by ninety degrees or some other amount along the center axis of the coupling device 1100 in order to present more length of cutting edge within the interior. It will also be noted that in this embodiment, the cutting edges of the blades 1102, 1104 are normal to the path through the lumen. By comparison, the cutting edge(s) of the blade 902 in FIG. 9 is angled from normal to the path through the lumen.

Figure 12:
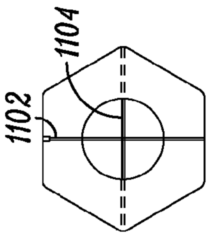
FIG. 12 shows an axial cross-sectional view of the coupling device viewed from the perspective indicated in FIG. 11.

FIG. 12 shows an axial cross-sectional view of the coupling device viewed from the perspective indicated in FIG. 11. As can be seen, the blades 1102, 1104 are offset by ninety degrees in this embodiment, although other orientations may also be employed.

Figure 13:
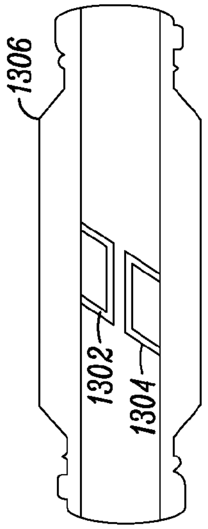
FIG. 13 shows a cross-sectional view of a coupling device with built-in cutting blades.

FIG. 13 shows a cross-sectional view of a coupling device with built-in cutting blades. In this embodiment, the blades 1302, 1304 are built into the interior wall of the coupling device 1306. Thus, while the blades of the preceding figures are generally removable and replaceable by withdrawing and inserting the blades into suitably positioned slits in the coupling device, the blades 1302, 1304 are affixed to the wall. This configuration may, for example, be conveniently used in a fully disposable coupling device or the like.

Figure 14:
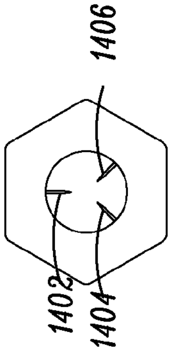
FIG. 14 shows an axial cross-sectional view of a coupling device with built-in cutting blades.

FIG. 14 shows an axial cross-sectional view of a coupling device with built-in cutting blades. In this embodiment, three blades 1402, 1404, 1406 are provided at various angles. As with the blades above, these blades may present cutting edges on either or both sides thereof.

Figure 15:
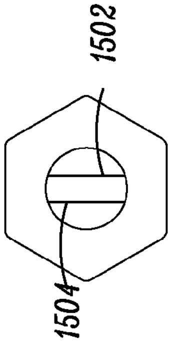
FIG. 15 shows an axial cross-sectional view of a coupling device with built-in cutting blades.

FIG. 15 shows an axial cross-sectional view of a coupling device with built-in cutting blades. In this embodiment, two parallel blades 1502, 1504 are employed.

It will be appreciated more generally from the many embodiments described above that numerous variations are possible for single and multi-blade configurations including permanent and/or removable blades, single and/or double edged blades, and so forth. All such variations as would be recognized by one of ordinary skill in the art are intended to fall within the scope of this disclosure.

Figure 16:
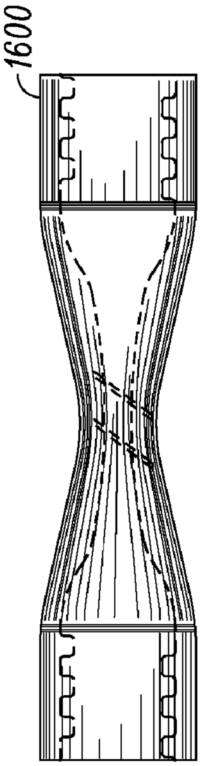
FIG. 16 shows a coupling device for syringes.

FIG. 16 shows a coupling device for syringes. The coupling device 1600 may be formed of a disposable material such as plastic, and may include a double-edged, angled blade integrated into an interior volume thereof. The coupling device 1600 may also include threaded connectors for attaching to syringes as generally described above.

Figure 17:
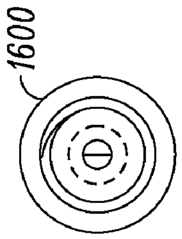
FIG. 17 shows an axial view of the coupling device of FIG. 16.

FIG. 17 shows an axial view of the coupling device of FIG. 16.

Figure 18:
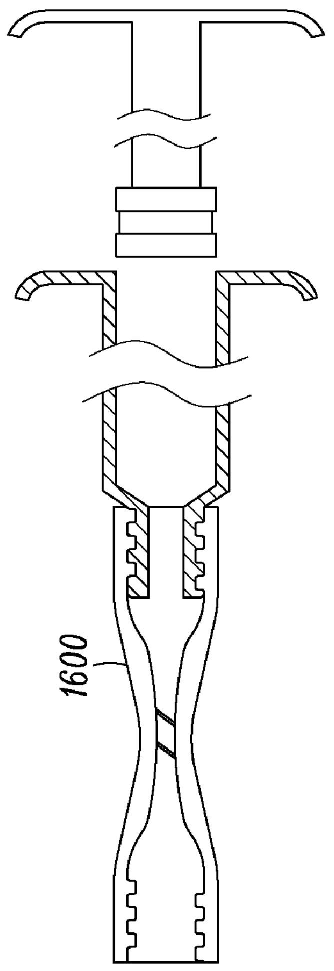
FIG. 18 shows a cross sectional view of the coupling device of FIG. 16.

FIG. 18 shows a cross sectional view of the coupling device of FIG. 16. It will be noted from FIG. 18 that the coupling device 1600 includes an interior volume that narrows or restricts around the cutting blade. This general design may advantageously increases the proportion of passing material that is directly exposed to the blade, which affect may be increased by narrowing the interior into, e.g., an oval shape with a major axis aligned to the blade. This general design may also serve to move material by the blade at a higher velocity than the plunger motion, thus providing an effective mechanical advantage to a user.

The systems and methods described herein may further be embodied as kits for harvesting, processing and injecting autologous injectable dermis. Such kits may be customized according to, e.g., the anatomical region for which supplementation is desired. Other arrangements of kit components may depend upon whether an entire disposable system is desired, or simply a small number of disposable components such as coupling devices and blades. In certain embodiments, the kits may generally include a harvesting device, a processing device, and a delivery device. More specific examples of certain kits are provided below, any of which may have packaging (such as individual, sterile packaging) adapted to a particular intended market or use.

For example, a kit may include a disposable blade harvesting knife, a meshing device to fragment autologous dermis, an autoclavable cutting transfer chamber that holds an assortment of disposable blades, (alternatively, the entire chamber and blades can be disposable with a plastic housing and single use blades), and injection needles of varying lengths and diameters, along with instructions for the use of the kit for tissue volume supplementation and any warning labels or other labels that might be required. A kit as disclosed herein may be suitable for combination with other pharmacological agents that could be added to the delivery device along with the autologous injectable dermis filler so that the pharmacological agent (e.g., a local anesthetic, an antibiotic or a vasoconstrictor) would be delivered into the tissues simultaneously with the filler. Similarly, many of the additives described above may be suitably packaged with kits for specific purposes.

In one aspect, a kit disclosed herein for processing injectable dermis includes two syringes; a blade; and a coupling device, the coupling device including a lumen and two connectors adapted to connect the lumen to the two syringes to form a continuous interior volume, and the coupling device adapted to support the blade in a position that presents at least one cutting edge of the blade across a path through the lumen.

The kit may further include a needle adapted to connect to one of the two syringes. The kit may include a skin graft harvesting knife. The kit may include a skin graft mesher. The kit may include scissors. The kit may be entirely disposable. The kit may include a blade holder that holds a plurality of blades. The blade holder may include an autoclavable cutting transfer chamber. The blade holder may be disposable.

In another aspect, a kit for processing injectable dermis includes at least one dermis harvesting tool; at least one dermis processing tool; and at least one live dermis injecting tool.

The dermis harvesting tool may include one or more of a hand held skin graft harvesting knife; a disposable skin graft harvesting blades; and mineral oil to facilitate harvesting. The dermis processing tool may include one or more of a skin graft mesher; a 3:1 mesh disposable carrier; a pair of mincing scissors; two pairs of microsurgical forceps to allow trauma-free handling; three pairs of 3 cc syringes; three 1 cc Luer Lock syringes; a disposable connecting cutting chamber with pre-attached intra-luminal blade(s); and a connecting cutting chamber that holds a plurality of blades. The connecting cutting chamber may include an autoclavable, re-usable device. The connecting cutting chamber may include a pre-fabricated plastic disposable device. The dermis processing tool may include a lumen and two connectors adapted to connect the lumen to Luer Lock syringes to form a continuous interior volume, the dermis processing tool adapted to support a blade in a position that presents at least one cutting edge of the blade across a path through the lumen. The dermis processing tool may include a coupling transfer connector adapted to facilitate mixing of injectable dermis with fat and other additives and/or materials. The coupling transfer connector may be adapted to connect to a 1 cc Luer Lock syringe for transfer of a substance thereto. The dermis injecting tool may include at least one blunt-tipped injection needle for injection of material from a 1 cc Luer Lock syringe. The at least one blunt-tipped needle may include a plurality of needles having luminal sizes from 14 gauge to 25 gauge. The at least one blunt-tipped needle may include a plurality of needles having lengths between 0.5 inches and 3 inches.

It will be understood that numerous other arrangements of kit components may be usefully provided without departing from the scope of this disclosure.

While particular embodiments of the present invention have been shown and described, it will be apparent to those skilled in the art that various changes and modifications in form and details may be made therein without departing from the spirit and scope of the invention as defined by the following claims, which are to be interpreted in the broadest sense allowable by law.

What is claimed is:

1. A scissor device comprising:

a pair of scissors including two blades, one of the two blades including a hole therethrough; and a connector adjacent to the hole, the connector adapted to couple with a syringe and secure the syringe in a position to deliver material through the hole, wherein the connector includes a Luer Lock connector welded to the one of the two blades.

2. The scissor device of claim 1 further comprising a plurality of pairs of scissors having progressively smaller holes through at least one blade thereof.

3. The scissor device of claim 1 wherein the one of the two blades includes a plurality of holes therethrough, each one of the plurality of holes having an associated connector, and the plurality of holes having a progressively smaller diameter.

4. The scissor device of claim 1 wherein the hole is substantially circular.

5. The scissor device of claim 1 wherein the scissor device is fabricated from stainless steel.

6. The scissor device of claim 1 wherein the scissor device is fabricated from a disposable plastic.

7. A scissor device comprising:

an inflow syringe including a plunger and a barrel; and a pair of scissors including two blades, one of the two blades including a hole therethrough, the hole coupled in a communicating relationship with the barrel of the inflow syringe through a Luer Lock connector to form a lumen between the hole and the barrel for passage of material therethrough, wherein the Luer Lock connector is welded to the hole.

8. The scissor device of claim 7, wherein the lumen is formed by a first lumen of the Luer Lock and a second lumen of the hole.

9. The scissor device of claim 7, wherein the hole is positioned near a cutting edge of the one of the two blades.

10. The scissor device of claim 7, wherein the lumen has an interior size between 1 mm and 3 mm.

11. The scissor device of claim 7, wherein a Luer Lock connector is formed of stainless steel.

12. The scissor device of claim 7, wherein a Luer Lock connector is formed of an autoclavable material.

13. The scissor device of claim 7, wherein the scissor includes a plurality of pairs of scissor blades.

14. The scissor device of claim 7 wherein the scissor device is fabricated from stainless steel.

15. The scissor device of claim 7 wherein the scissor device is fabricated from a disposable plastic.

16. The scissor device of claim 7 wherein the one of the two blades includes a plurality of holes therethrough, each one of the plurality of holes having an associated connector, and the plurality of holes having a progressively smaller diameter.

17. A scissor device comprising:

an inflow syringe including a plunger and a barrel; and a pair of scissors including two blades, one of the two blades including a plurality of holes therethrough, one of the plurality of holes coupled in a communicating relationship with the barrel of the inflow syringe to form a lumen between the hole and the barrel for passage of material therethrough, and one or more other ones of the plurality of holes each having an associated connector and each having a progressively smaller diameter.

18. The scissor device of claim 17 further comprising a Luer Lock connector coupling the one of the plurality of holes to the barrel of the inflow syringe.

19. The scissor device of claim 17 wherein the pair of scissors if fabricated from stainless steel.

20. The scissor device of claim 17 wherein the lumen has an interior size between 1 mm and 3 mm.

* * * * *